United States Patent
Vittorio

(10) Patent No.: US 10,275,531 B2
(45) Date of Patent: *Apr. 30, 2019

(54) MEDICAL CONTENT SEARCH AND RESULTS

(71) Applicant: Steven Michael Vittorio, Gainesville, FL (US)

(72) Inventor: Steven Michael Vittorio, Gainesville, FL (US)

( * ) Notice: Subject to any disclaimer, the term of this patent is extended or adjusted under 35 U.S.C. 154(b) by 456 days.

This patent is subject to a terminal disclaimer.

(21) Appl. No.: 14/521,149

(22) Filed: Oct. 22, 2014

(65) Prior Publication Data

US 2015/0112979 A1    Apr. 23, 2015

Related U.S. Application Data

(60) Provisional application No. 61/894,378, filed on Oct. 22, 2013, provisional application No. 61/979,555, filed on Apr. 15, 2014.

(51) Int. Cl.
| | | |
|---|---|---|
| *G06F 17/30* | (2006.01) | |
| *G09B 5/02* | (2006.01) | |
| *G09B 5/04* | (2006.01) | |
| *G06F 19/00* | (2018.01) | |

(52) U.S. Cl.
CPC .... *G06F 17/30867* (2013.01); *G06F 17/3053* (2013.01); *G06F 19/324* (2013.01); *G09B 5/02* (2013.01); *G09B 5/04* (2013.01)

(58) Field of Classification Search
None
See application file for complete search history.

(56) References Cited

U.S. PATENT DOCUMENTS

| | | | |
|---|---|---|---|
| 6,626,959 B1 * | 9/2003 | Moise | G06F 17/246 |
| | | | 715/210 |
| 6,987,945 B2 | 1/2006 | Corn et al. | |
| 7,526,475 B1 | 4/2009 | Verstak et al. | |
| 8,001,141 B1 * | 8/2011 | Bar | G06Q 30/06 |
| | | | 707/723 |
| 8,352,467 B1 | 1/2013 | Guha | |
| 8,392,244 B1 * | 3/2013 | O'Halloran | G06F 19/328 |
| | | | 705/14.1 |

(Continued)

FOREIGN PATENT DOCUMENTS

WO    WO-2014071033 A1    5/2014

OTHER PUBLICATIONS

International Search Report in International Application No. PCT/US2016/028080, filed Apr. 18, 2016.

(Continued)

*Primary Examiner* — Marc S Somers
*Assistant Examiner* — Edward Jacobs
(74) *Attorney, Agent, or Firm* — Saliwanchik, Lloyd & Eisenschenk

(57) ABSTRACT

A search request for medical content can be initiated by a user, and the medical content that is relevant to the search request can be identified. The identified medical content can be ranked based on the number of times the content has been referenced as well as by the healthcare provider that referenced the medical content. The relevant identified medical content can then be displayed in an ordered list that is ordered based on the number of times the content has been assigned.

20 Claims, 4 Drawing Sheets

(56) References Cited

U.S. PATENT DOCUMENTS

| | | | |
|---|---|---|---|
| 8,417,698 B2* | 4/2013 | Yoo | G06F 17/30867 |
| | | | 707/732 |
| 8,676,828 B1 | 3/2014 | Agarwal et al. | |
| 8,805,814 B2 | 8/2014 | Zijlstra et al. | |
| 2002/0078045 A1* | 6/2002 | Dutta | G06F 17/30675 |
| 2003/0125983 A1* | 7/2003 | Flack | G06Q 50/22 |
| | | | 705/2 |
| 2003/0144877 A1* | 7/2003 | Goldmann | G06F 19/325 |
| | | | 705/2 |
| 2004/0153343 A1* | 8/2004 | Gotlib | G06F 19/324 |
| | | | 705/3 |
| 2004/0162772 A1* | 8/2004 | Lewis | G06Q 30/04 |
| | | | 705/34 |
| 2005/0026131 A1 | 2/2005 | Elzinga et al. | |
| 2005/0228593 A1* | 10/2005 | Jones | G06Q 10/10 |
| | | | 702/19 |
| 2007/0185864 A1 | 8/2007 | Budzik et al. | |
| 2008/0046286 A1* | 2/2008 | Halsted | G06Q 50/22 |
| | | | 705/2 |
| 2008/0208624 A1* | 8/2008 | Morita | G06Q 10/00 |
| | | | 705/2 |
| 2009/0106799 A1 | 4/2009 | Park et al. | |
| 2009/0182725 A1 | 7/2009 | Govani et al. | |
| 2009/0271379 A1* | 10/2009 | Bakalash | G06F 17/30457 |
| 2009/0281988 A1* | 11/2009 | Yoo | G06F 17/30867 |
| 2010/0179828 A1* | 7/2010 | Kelly | G06F 19/3456 |
| | | | 705/3 |
| 2010/0268552 A1* | 10/2010 | Schoenberg | G06Q 30/04 |
| | | | 705/3 |
| 2011/0004588 A1* | 1/2011 | Leitersdorf | G06F 17/30864 |
| | | | 707/711 |
| 2011/0010366 A1* | 1/2011 | Varshavsky | G06F 17/30864 |
| | | | 707/732 |
| 2011/0055189 A1 | 3/2011 | Effrat et al. | |
| 2011/0144908 A1 | 6/2011 | Cheong | |
| 2011/0212430 A1 | 9/2011 | Smithmier et al. | |
| 2012/0005201 A1* | 1/2012 | Ebanks | G06F 17/30867 |
| | | | 707/728 |
| 2012/0066256 A1 | 3/2012 | Ramamurthi et al. | |
| 2012/0117088 A1* | 5/2012 | Kawakami | G16H 50/70 |
| | | | 707/749 |
| 2012/0245952 A1* | 9/2012 | Halterman | G06Q 10/10 |
| | | | 705/2 |
| 2013/0040275 A1 | 2/2013 | Gowda | |
| 2013/0095464 A1 | 4/2013 | Ediger et al. | |
| 2013/0262142 A1* | 10/2013 | Sethumadhavan | G06Q 50/24 |
| | | | 705/3 |
| 2013/0280682 A1* | 10/2013 | Levine | G09B 25/00 |
| | | | 434/236 |
| 2014/0006930 A1 | 1/2014 | Hollis et al. | |
| 2014/0058753 A1* | 2/2014 | Wild | G06Q 50/01 |
| | | | 705/3 |
| 2014/0143232 A1* | 5/2014 | Abe | G06F 17/30991 |
| | | | 707/722 |
| 2015/0154646 A1* | 6/2015 | Mishra | G06Q 50/24 |
| | | | 705/3 |
| 2015/0248484 A1 | 9/2015 | Yu et al. | |

OTHER PUBLICATIONS

International Search Report in International Application No. PCT/US2014/061806, filed Oct. 22, 2014.

* cited by examiner

MEDICAL CONTENT SEARCH AND RESULTS

CROSS-REFERENCE TO RELATED APPLICATIONS

This application claims the priority benefit of U.S. Provisional Application Ser. No. 61/894,378, filed Oct. 22, 2013, and U.S. Provisional Application Ser. No. 61/979,555, filed Apr. 15, 2014, both of which are incorporated herein by reference in their entirety.

BACKGROUND

People sometimes turn to the Internet to find out more about the options for treating their medical condition or symptoms. Searching for medical content and information over the Internet can be difficult because it is not easy to determine whether a medical device, drug, therapy, or treatment is most appropriate for a given set of medical problems or symptoms. Although there are a number of websites that purport to provide medical information, a search of this content is generally conducted directly using key terms input to a search bar.

Unfortunately, it is not always possible to determine which of a number of results would be the most likely one to be helpful in ameliorating a given medical problem. Sometimes results are ranked according to relevancy, but the relevancy ranking may only be a function of a number of times a term is found in the text of an article about a medical problem. In some cases, there may be reviews of the medical content which can help inform the decision. However, the trustworthiness of the suggestion or review may be difficult to determine.

BRIEF SUMMARY

Systems and techniques for facilitating medical content search and results are described.

A method of facilitating medical content search and results can include, for example, identifying a plurality of medical content in response to receiving a search query, identifying a number of times each medical content of the plurality of medical content has been referenced by healthcare providers, and generating a search result of the plurality of medical content that is ordered based on the number of times each medical content has been referenced.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1:
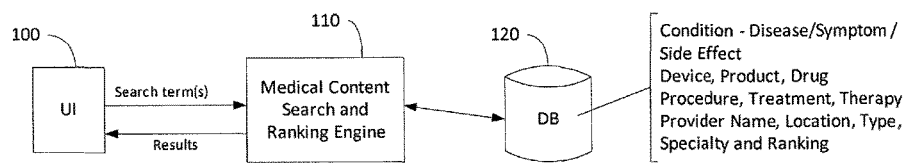
FIG. 1 illustrates an operating environment in which embodiments may be implemented.

Systems and techniques for facilitating medical content search and results are described. The medical content can be presented in a manner that indicates trustworthiness or relevancy based on the frequency of reference (e.g., purchase, use, prescription, or recommendation) by a healthcare provider. By providing searchers of medical content with information indicating the number of actual uses of, for example, a medical device, pharmaceutical, or therapy, the searcher may better evaluate the usefulness of the search results.

The medical content being referenced can include, for example, medical devices, medical products, pharmaceuticals, medical procedures, medical therapies, and medical treatments. The various kinds and categories of medical content may be known herein as "content types." Individual instances of medical content—e.g., a particular product like a pacemaker—may be sometimes known as an "item of medical content."

The healthcare provider referencing the medical content can include, for example, a hospital or other medical facility, doctor or other healthcare professional, and a pharmacy. A medical facility can include, for example, a hospital, clinic, outpatient surgical center, practitioner's office, urgent care facility, medical school, medical institution, mobile care center, physical therapy center, laboratory, diagnostic center, medical research center, gymnasium, and animal hospital. A healthcare professional may be, for example, a medical doctor, surgeon, specialist, nurse, nurse-practitioner, physician assistant, dentist, psychologist, psychiatrist, physical therapist, rehabilitation therapist, certified trainer, optometrist, osteopath, chiropractor, and veterinarian. The various kinds and categories of healthcare providers may be known herein as "provider types" or "healthcare provider types."

A healthcare provider may reference medical content in several ways, some non-limiting examples of which are described below. For example, a healthcare provider may purchase a medical device or medical equipment for use in a medical facility or medical procedure. A healthcare provider (such as a doctor) may use a medical therapy, medical device, medical procedure, or medical treatment on a patient or in a medical facility. A healthcare provider may prescribe a drug or non-drug therapy to a patient to ameliorate an ailment. A healthcare provider may even recommend a lifestyle change or other course of action, such as that the patient intake less salt, to assist in treating a symptom or disease.

An instance of "referencing" (e.g., purchasing, using, prescribing, and recommending) a medical content may be counted such that ranking of the references associated with a disease, symptom, or side effect are possible. A brief example may be illustrative: A patient searches for the ailment "hypertension" using the described systems and techniques. The search may return ordered medical content results showing that, for example, 99 healthcare providers recommend reducing salt intake, 95 recommend stopping smoking, 91 recommend more exercise, and 48 prescribe the hypertension-reducing drug X and 28 recommend the hypertension-reducing drug Y. Presenting results in this manner may assist the patient in evaluating therapeutic options by referencing the actual behavior of healthcare providers. "Using" may include "wearing," as when a healthcare professional wears a particular brand of gloves or other personal protective gear; using may also include conducting, administering, or employing in some way; for example, a hospital might use a particular kind of anti-microbial mousepad for its computing systems, or particular software for handling patient intake data.

The manner that a medical content is referenced (sometimes known herein as a "reference type") may in some implementations affect how the medical content is ranked and/or counted. For example, certain medical products, procedures, treatments, therapies, or drugs may be indicated as "prescribed," whereas others may be suggested as "recommended." Some products may be medical supplies or techniques purchased or used by a facility. In some implementations, all or a subset of referenced medical content are included as part of the results. In some implementations, only the prescribed content are included as part of the results. In other implementations, only the recommended content are included as part of the results. In some implementations, the manner in which the medical content is referenced is indicated as metadata associated with the particular content.

In some cases, a weight may be assigned to the medical content (for the rankings) based on the manner in which the content is referenced. In some cases, no distinction based on the manner in which the content is referenced is made in the rankings. In other cases, "prescribed" may be weighted over "recommended" content, for example. In yet other cases, a distinction may be provided between "prescribed," "recommended," "purchased," and "used" medical content through use of an indicator in the search results. Accordingly, it should be understood that the content ranking may be based on the manner in which content is referenced by a healthcare provider; and when reference is made to "referenced" medical content any combination of medical content used, purchased, prescribed, recommended, or otherwise utilized for a disease or symptom may be included in all permutations.

In some implementations, only "prescribed" content is presented for a user. In some implementations only "recommended" content is presented for a user. In some cases, only "purchased," or only "used" content may be presented for a user. In some implementations, any combination of purchased, used, prescribed, or recommended content may be presented for a user. In some implementations where medical content having multiple types of reference are presented to the user, the system may be agnostic about how the content is referenced and may present results as if there is no difference between the types of reference. In some implementations where more than one type of referenced content is presented to the user, the manner in which the content is referenced might not affect how the content is ranked, but can be indicated to the user so that the user knows whether the content was purchased, used, prescribed, or recommended by a healthcare provider. One way of indicating the manner in which the content was referenced is to include a particular icon, popup, or other indication in association with an indicator of the healthcare provider (or other level of granularity relevant to the healthcare provider) that referenced the content.

In some implementations where content having multiple reference types are presented to the user, the manner in which the content is referenced can affect the rankings. For example, each "prescribed" reference to a piece of content may be weighted differently than each "recommended" reference to that piece of content. As another example, the number of prescribed references to an item of medical content may be used as a tie-breaker when two pieces of content have a same number of total references, but differing numbers of prescribed references (e.g., both pieces of content have 10 references, but one was referenced as prescribed 7 times and the other was indicated as prescribed only 6 times—the remaining references being recommendations). Modifying rankings through weighting or tiebreaking in accordance with prescribed and recommended reference types of course extends to other reference types (e.g., purchased and used).

In some implementations, the type of medical content may affect the rankings through weighting. For example, when multiple types of medical content are presented to the user (e.g., mixed results of drugs, medical devices, procedures, and therapies), one or more types of medical content may be weighted differently than other types. For example, a medical device may be weighted higher than a drug therapy.

The information about medical content referenced by a healthcare provider may be gathered from a variety of medical content referencing data sources. Sources of referencing data may be a medical facility or healthcare provider information system, such as a system used to chart patients, patient outcomes, or healthcare professionals' activities. Medical insurance databases may also be sources of referencing data. Medical device or pharmaceutical sales and inventory databases may also be sources of referencing data for medical content. Government databases, such as may be provided by the Centers for Disease Control, may be sources. Research databases containing demographic or epidemiological information may be sources, as well as databases containing genetic results such as associations between genomes and disease prevalence. Consumer data provided by data brokers from ad tracking or other data mining activity may also be sources. In some cases, information about individual patients may be masked or anonymized to ensure patient privacy and compliance with medical privacy statutes. The medical content referencing data sources described above are illustrative only and should not be considered as limiting of the types and varieties of information systems that may be a source of medical content referencing data by healthcare providers.

FIG. 1 illustrates an operating environment in which some embodiments may be implemented. Referring to FIG. 1, a user may conduct a search of medical content through a user interface (UI) 100. The search can be conducted on diseases, conditions, symptoms, side effects, medical therapies, medical devices, medical products, pharmaceuticals, drugs, properties of drugs and pharmaceuticals, medical procedures, medical treatments, or a combination of one or more of these categories. The areas for the search may be specified by the medical content search and ranking engine 110 (e.g., via a drop-down menu) or may include free-form input provided by the user via the UI 100 (e.g., via a search bar).

Figure 2:
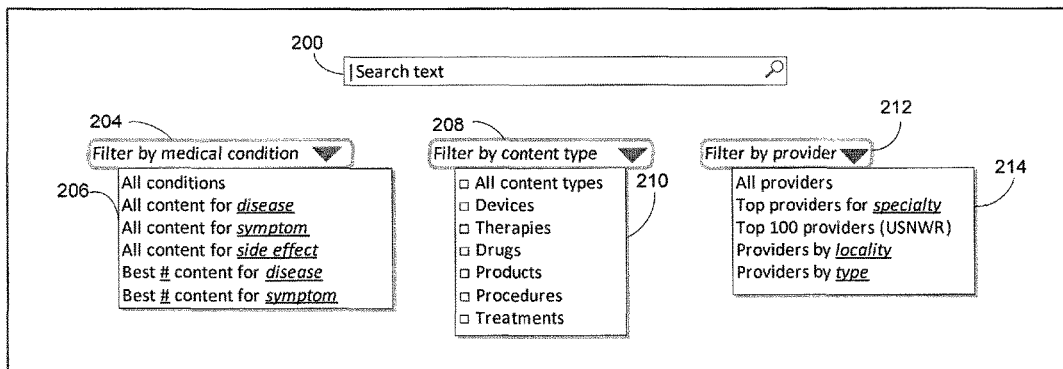
FIG. 2 illustrates an example user interface of a search page.

The user interface may include features as illustrated in FIG. 2. As shown in FIG. 2, an input field 200 can be provided for receiving a search query for medical content. As noted, the input field 200 may allow searching of a wide variety of medical content, as well as searching medical content by diseases, conditions, symptoms, or side effects to which medical content may be associated.

In some implementations, users do not need to do a search to access the content as the content may be listed in a default or otherwise optimized manner before a specific search is entered by the user. In some implementations, an ordered listing of content can be presented on a landing page (e.g., "home page") of a medical content listing website rendered in a user's browser application (and providing a user interface to the medical content search and ranking engine). The default ordered listing may be, for example, of content for the top diseases, conditions, or side effects ordered by the frequency or incidence of the disease, condition, or side effect within a given population (as known from the database or other structured data stored on a resource for the medical content search and ranking engine). A default ordered listing may also be, for example, the top prescribed, recommended, purchased, or used medical content for a given population. In some cases, demographic characteristics of the user may be used to determine the relevant population.

In some implementations, user-adjustable filters may be used to narrow, refine, or reorder the results before a search is conducted or after the search is conducted.

A "filter by medical condition" 204 can provide filtering options 206 such as, but not limited to, enabling a search of content for all conditions, all content for a specified disease, all content for a specified symptom, all content for a specified side effect, a designated number of highest ranked content for a specified disease (e.g., "top 10 content for hypertension"), and a designated number of highest ranked content for a specified symptom (e.g., "top 25 content for headache") as some examples. In some cases, the disease, symptom, or side effect being filtered may be indicated by the text in the search text input field 200.

A "filter by content type" 208 can provide filtering options 210 such as—but not limited to—enabling a search of all content types, or a search of one or more individually selected content types, for example medical devices, therapies, drugs, products, procedures, and treatments. Sub-types are also possible, including, but not limited to, controlled substances, over-the-counter products, herbal substances, in-patient procedures, and out-patient procedures. In some embodiments, sub-types may include sub-components or properties of content types. For instance, pharmaceuticals may be filtered by such further sub-components as "active ingredient" so that, for example, particular classes of chemical the user is allergic to may be excluded. In another instance, if medical cannabis is returned as a result after a search for "epilepsy," additional filtering options may filter the cannabis types by properties such as type of administration or formulation (e.g., dried leaf/flower, oil, pill form, chewable, extract, concentrate), botanical categorization (e.g., leaf), strength (perhaps because a milder cannabis may be needed for a child with epilepsy). Other sub-type filters may be envisioned depending on content type.

A "filter by provider" 212 can provide filtering options 214 such as, but not limited to, enabling a search of all providers (e.g., medical facilities and healthcare professionals), for top providers in a designated specialty (e.g., "top cancer hospitals" or "top oncologists"), for the top 100 (or other "top" number) providers according to a designated ranking service (e.g., "top 100 providers from the U.S. News and World Report (USNWR) rankings"), for providers by designated locality (e.g., "providers in Florida"), and for providers by a designated type (e.g., "outpatient orthopedic surgical centers") as some examples. In some cases, filtering can be according to insurance policies.

Other filter types (not shown in FIG. 2) are also possible, enabling further filtering of some results. In some embodiments, available filter options may be determined or dynamically redefined by prior filter selections, as for example when selection of a "symptom" filter surfaces an additional filter based on different symptom names or categories. In some cases, a filter selection may initiate the display of an additional interface or interface element. For example, a "product" content type may initiate the display of an interface for navigating product subcategories, such as "pacemakers," "stents," or "artificial valves."

Of course, other designations may be provided and even natural language queries may be used in certain implementations. The described search and ranking engine may be accessible via a personal assistant such as Siri® available from Apple Inc., Google Now™, or Cortana® available from Microsoft Corp. Queries may be input through voice commands or by touch or text or other input. The manner of applying the filter(s) may be any suitable tool bar, input field, or menu for providing the information.

Returning to FIG. 1, search terms entered via the user interface 100 are used by a medical content search and ranking engine 110 to search a database (DB) 120. The database 120 can include structured information regarding medical content. A wide variety of medical content information may be stored, some of which may support the use of filtering categories described above. The database can be generated, for example, based on data provided by healthcare providers, insurance companies, consumer data companies, medical device manufacturers, medical product suppliers, pharmacies, and medical researchers.

The medical content search and ranking engine 110 can use the search terms provided via the user interface 110 to identify relevant medical content from the database 120. The identified medical content can be ranked by the medical content search and ranking engine 110 based on the number of times the content has been referenced.

Characteristics of the healthcare provider that referenced the medical content may also influence the rankings (through filtering and/or weighting the number). In some implementations, the number of references to a particular medical content item may be counted per provider, or may be subdivided by medical facility and healthcare professional.

The relevant identified medical content can then be displayed at the user interface 100 in an ordered list that is ordered based on the number of times the content has been referenced. In some cases, an indication of the number of times the content has been referenced can be provided. In some cases the indication of the number of times the content has been referenced may be tabulated per healthcare provider. The listing within the UI 100 can show trending, such as new surgical techniques or medications. Recent trends can affect the weighting—for example, bypass surgeries may have dominated 20 years ago, but angioplasty and stent implants are the dominant trend today. The relevant identified medical content can also reflect recent FDA approvals.

In one embodiment, an initial search query may not be through the UI 100 and, instead, is a result of the request from a web browser to return information from a website (providing the UI 100) at a particular uniform resource location (URL). For example, when a user enters a URL in their web browser to go to the website specifically covering a designated disease (e.g., "lupus"), the hypertext language protocol (HTTP) request for the URL can initiate a query (e.g., based on a default search query in the string or as a field of the request) by the search and ranking engine 110 and those results can be rendered in the web browser as a default result list that can be part of the UI 100 before a user enters a specific query.

In one embodiment, an initial search query may not be through a UI 100 and, instead, is the result of a request from a mobile device application connected through a mobile device to a biometric sensor. For example, a user may be wearing one or more biometric sensors to detect, e.g., pulse, blood oxygen, airflow, body temperature, galvanic skin response, patient position, or heart rhythms. The biometric sensors may be connected to a mobile device running an application that may send queries to the medical content search and ranking engine 110 (for example, via HTTP, as noted above). Search results of medical content may be presented to the user via UI 100 when an out-of-boundary biometric condition is detected by the application via the biometric sensors. As a specific example, a detection of an erratic heartbeat or rhythm by a biometric sensor might cause the mobile device application to request information about the symptom "arrhythmia" and prompt the display of results having various conditions and ameliorative options for that symptom. An example of a supporting user interface is shown in FIG. 3C. Techniques for reading biometric sensors from a mobile device are supported by application frameworks such as the "e-Health Sensor Platform for Raspberry Pi."

In one embodiment, a user's medical history may be stored in DB 120. The user may enter the medical history directly through an interface 100 of the medical content search and ranking engine 110, or the user may select an option to interchange data with another health database storing the user's medical history. An example of a commercial medical history storage service that may allow data interchange is "MyMedicalRecords.com." A user's stored medical history may be used, in some cases, to assist in identifying relevant medical content related to the search term. A user's medical history may also provide information to the ranking engine to shape or inform the weights assigned to medical content references, provide additional filters, or provide relevant information for tie-breakers. For example, if it is known (via the stored medical history) that a user is allergic to painkillers containing codeine, then drugs containing codeine may not be presented as medical content in relation to a symptom or condition search. As an alternative example, if a user's medical history indicates that he or she has difficulty awakening from the anesthesia given for surgery, medical content for surgical procedures may be weighted lower than non-surgical treatment options, even when some surgical medical content may be weighted higher for patients not having difficulties with anesthesia.

Figure 3A:
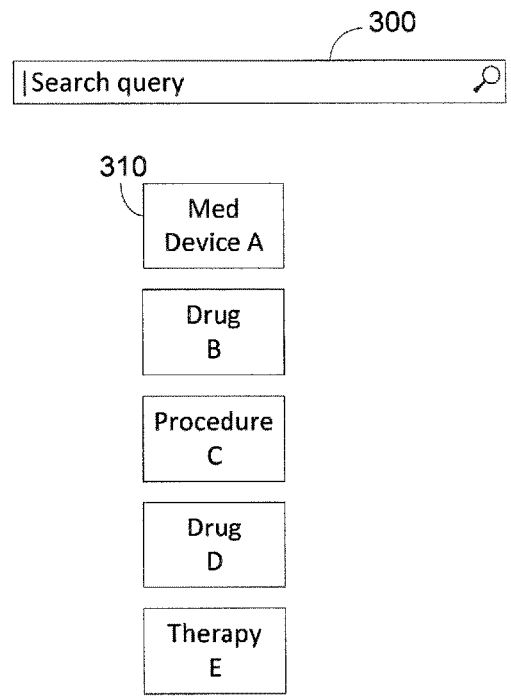
FIGS. 3A-3D illustrate example search result ordered list presentations.
Figure 3B:
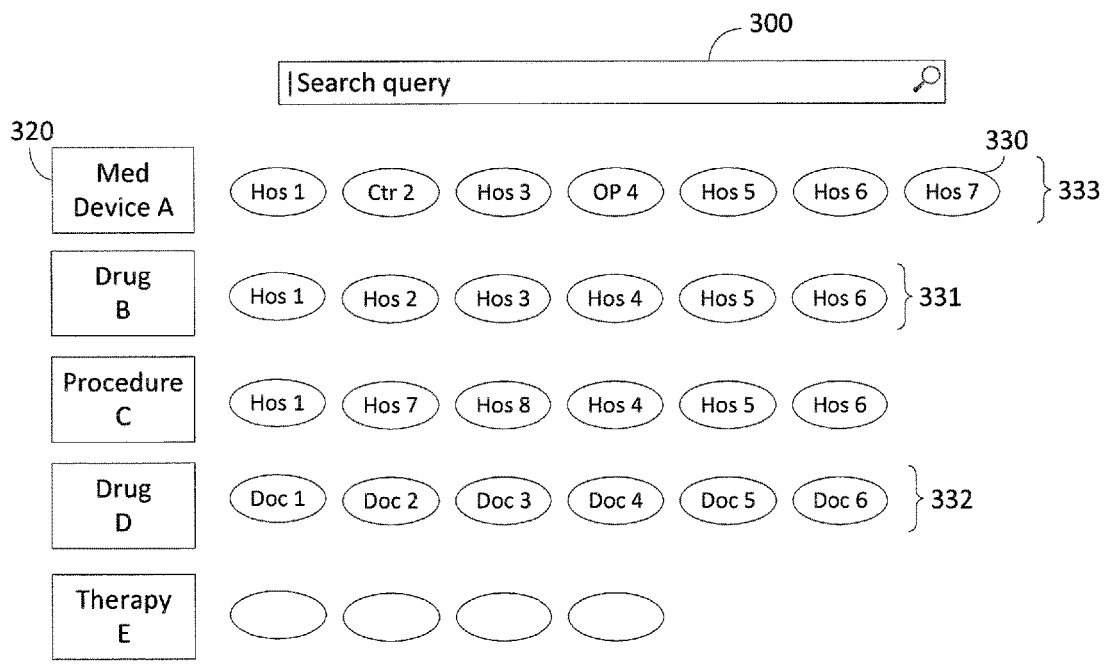
Figure 3C:
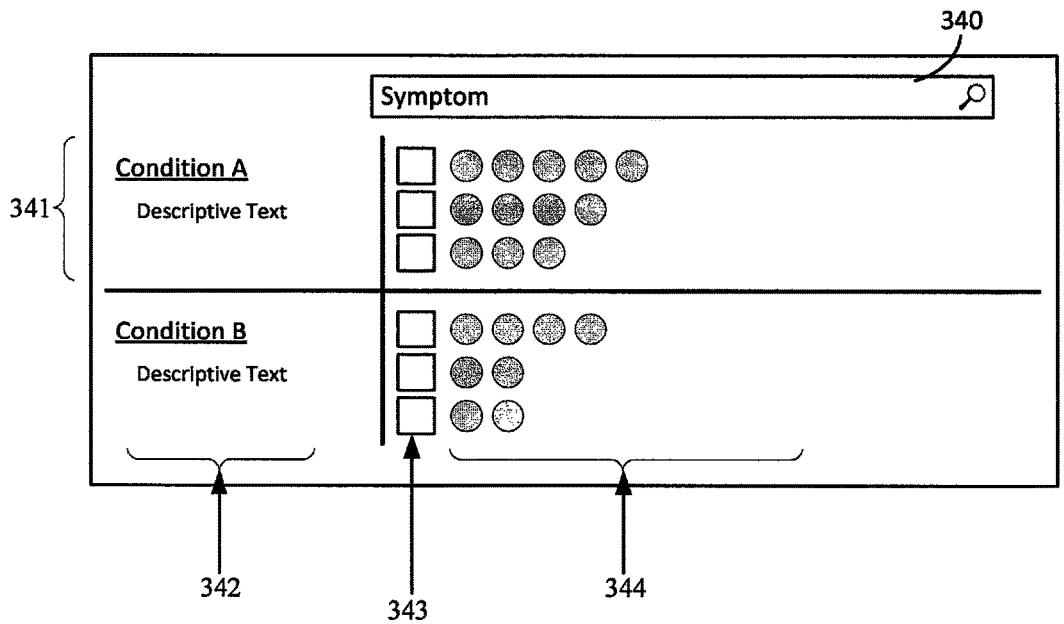

FIGS. 3A and 3B illustrate example search result ordered list presentations. Several kinds of medical content are exemplified in FIGS. 3A-3B, but should not be considered as limiting. In response to receiving a search query in the search input field 300 of a user interface, an ordered listing of medical content can be displayed. In FIG. 3A, the medical content 310 may be presented in a list from most referenced to least referenced. Additional filters (such as shown in FIG. 2) may be applied to further narrow the listing.

Results of the search can be presented with indicators of the number of providers that referenced the medical content, a specific indicator (e.g., a badge or icon) for each provider that references the content, an individual healthcare professional that references the content within a facility, a specific disease or symptom that the content is targeted toward, a demographic attribute, credentials of a healthcare provider, the level or severity of side effects that may be caused by the treatment option represented by the content, and/or other information that can support the ranking of the medical content (e.g., provide information regarding the relevancy) and/or provide additional information that a user may use to select an item of content or obtain additional information.

For example, referring to FIG. 3B, the medical content 320 may be presented with an indicator 330 of the providers that referenced the content. In one implementation using an indicator (e.g., icon or badge) for a particular medical facility provider that referenced an item of content, the indicator can be used once per content even if the content is referenced by multiple healthcare professionals at the facility 331. Thus, each indicator represents that a medical facility has referenced the content at least once. In another implementation, the indicator for a particular facility that referenced a content item may be used to represent each reference to the content so that multiple indicators for that particular facility may be shown for the referenced content when multiple healthcare professionals at that facility reference the content. In some cases, each indicator may show a healthcare professional's name or other information 332. In another implementation, a counter may be displayed on the healthcare provider indicator to indicate the number of times the content was referenced.

As described with respect to FIG. 2, results can be filtered. In one scenario, the results are filtered by provider or a select grouping of providers. For example, the results can be filtered to show rankings based on ranking services of top healthcare providers, by providers in a particular geographical locality, by a user-specified provider or providers, by a top number of providers in a specialty area (as ranked by a provider ranking system), by a type of provider, or by other provider-related configuration.

As illustrated in FIG. 3B, each item of medical content can include one or more indicators of the healthcare provider referencing the content. The indicators can be presented in order (e.g., left to right) of the provider's ranking on the U.S. News and World Report medical provider ranking system, Top 100 Hospitals Website, Hospital Webometrics, or other healthcare provider ranking system. Sometimes, healthcare providers may be of mixed type, for example showing indicators for hospitals, surgical centers, and outpatient facilities with respect to the same content 333. In some cases, whether indicators are shown in mixed mode may depend on the type of content (e.g., whether the content is a procedure, drug, device, therapy, etc.). In some embodiments, healthcare providers may be of a single type designated by the user in the search and filtering interface of FIG. 2. In some cases, individual healthcare professionals may be grouped together by their facility to create a single indicator badge. In some embodiments, the indicator badges may show the name (or other details) about a referencing healthcare professional. In some embodiments, selecting a healthcare facility indicator badge (e.g., a hospital) may cause additional interfaces to be rendered that display the individual healthcare professionals within the facility who prescribed, recommended, or used the medical content.

In some implementations, when multiple medical content (e.g., devices, drugs, procedures, therapies) within the results have a same number of providers that reference the content, the content having a same number of references may be presented in alphabetical order. In other implementations, the content may be presented in reverse chronological order, the results being weighted for recency of reference.

In some implementations, various mechanisms may be used to break ties between content that may have the same rankings (or are the same within a designated range). In some cases, the ranking order of tied results may be presented based on a ranking system of the healthcare providers that reference the content, such as the U.S. News and World Report. As noted, other ranking systems or sources may be used.

Another kind of tie-breaking mechanism that may be used to sort equally-ranked content is the content type (or subtype) of the medical content. For example, drugs may be prioritized above surgical procedures as preferential in some cases. Certain means of administration may be prioritized above other types, such as a preference for oils containing cannabis to dried-leaf forms.

Another type of tie-breaker that may be used refers to the credentials of the healthcare provider (medical facility or healthcare professional). For example, some healthcare professionals are board certified in particular specialties such as "internal medicine." Thus, ties may be effectively broken among content by considering the board certification/specialty status of healthcare professionals in comparison to the content referenced by individuals without board certification status. As a specific example, if a medical device and a drug are tied in the number of references received, but the drug received more prescriptions by board certified professionals, the drug may be ranked higher than the medical device.

Another type of tie-breaking mechanism may consider the incidence of side-effects caused by the medical content. Side-effect data may be stored in database 120 and accessed and analyzed by the medical content search and ranking engine 110. Among the side-effect data that may be stored in database 120 are the type, severity, and frequency of side-effects. Any or all of this side-effect data may be a factor in ranking a given item of medical content with respect to other medical content. For example, a tie between two items of medical content might be broken based a lower frequency of side effects in one content. An aspect of side-effect data may sometimes be a consequence related to the strength of the dosage of a substance; this might include not only higher dosages of typical pharmaceuticals, but also differing dosage properties of different types of botanical or herbal treatments (e.g., different variants of cannabis may have different strengths per mass unit).

It should also be noted that provider rankings and credentials, medical content type, and side-effect data as described with respect to tie-breaking mechanisms may also be used as weighting factors (as described above) to minimize or strengthen the numerical count of an individual reference.

In addition, one or more tie-breaking mechanisms may be applied to the listings of the results where a first tie breaking method does not break all the ties. As a non-limiting illustrative example, the ranking or credentials of the referencing provider may be first considered to break ties within the same ranked content. Any remaining ties may be broken by type of medical content or incidence of side-effects.

In some implementations, a user's option selection or user's medical history may be considered in choosing a tie-breaking mechanism. For example, if it is known via a user's medical history data stored in a DB 120 that the user has an allergy to a specific drug or substance, a "drug" medical content may be ranked lower than a surgical option. As another example, if a user has selected an option via a user interface 100 element to favor drug therapies over surgical options as medical content, a drug medical content may be shown above an equally-referenced surgical option.

Indicators may show other kinds of ranking criteria for medical content. Indicator types might include, for example, the type of reference (e.g., prescribed, recommended, used, purchased), healthcare professional name, specialty, board certification, geographic locality, and ranking organization (e.g., USNWR) indicators may be shown in some cases, depending on the criteria for ranking. In some cases, more than one indicator type may be shown, and the indicators may be grouped by type. Groups of badges may include, for example, groups for the medical facilities, healthcare professionals, and specialties referencing the content.

The user may sometimes desire to sort or filter results differently after the search results have been displayed in the search results list presentation. In some embodiments (not shown in FIG. 3B), user interface elements displaying additional filters can allow a user to group or select/deselect content types, provider types, reference types, or other filter criteria from the results on the search results list presentation.

FIG. 3C shows an example ordered search result list presentation that may be used in some implementations. An interface is shown in FIG. 3C that may be appropriate for displaying search results for a designated symptom indicated by a search term, filter, or interpreted from a biometric sensor device. The interface in FIG. 3C shows search results grouped by condition first, and then by ordered content with indicator badges.

The conditions displayed may be selected and ordered by likelihood that the symptom search term relates to a given condition or disease. Information about a symptom's probability of relationship to a condition may be informed by accessing an existing medical diagnostic system (for example, the WebMD® "Symptom Checker"). A probability of association between a symptom and a condition may in some cases be informed by the reference counting data recorded by the medical content search and ranking system.

In the figure, the results for an example search of conditions and content related to a symptom 340 are shown. Content is grouped by condition 341, which may have such interface elements as a condition name and/or descriptive text 342. Conditions may in some cases be ordered by likelihood that the symptom relates to the condition. In another area of the interface, a list of content 343 may be presented for each condition 341 that is ordered in accordance with the techniques disclosed herein. Each content 343 may show a series of indicator badges 344 indicating information about the referencing provider (or other information).

Figure 3D:
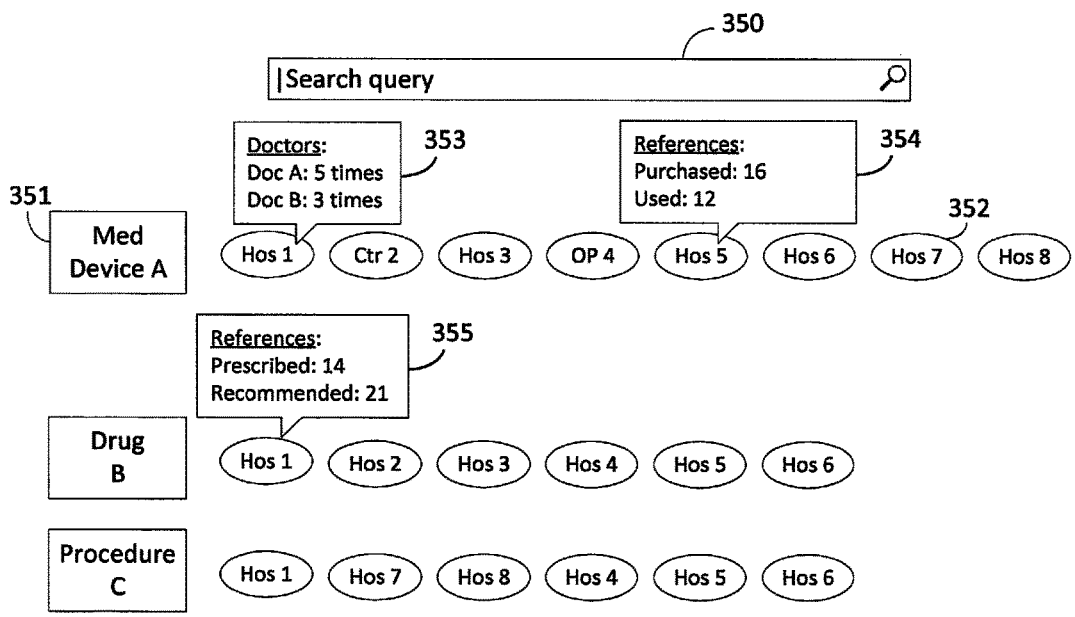

FIG. 3D illustrates an example ordered search result list presentation that may be used in some implementations. The example in FIG. 3D shows search query results of medical content with indicator badges and indicator popups. The search query 350 returns several search results of medical content 351. Each medical content result displays one or more indicator badges 352 of hospitals, doctors, or medical facilities.

Indicator popups (353, 354, 355) may show additional information about the selection criteria for an indicator badge, including such information as the individual doctors at a medical facility who referenced the medical content, or the number of references of a reference type. The indicator popups may show information that is appropriate or relevant both to the medical content type, the reference type, and the nature of the indicator badge. For example, in the figure, "Medical device A" was referenced by two individual doctors ("Doc A" and "Doc B") at "Hospital 1" for a total of 5 and 3 times, respectively 353. The indicator popup for "Hospital 5" 354 shows the information divided by reference type indicating the number of times the "Hospital 5" purchased and used "Medical Device A" 351. "Drug B" has a different indicator popup for "Hospital 1" 355, reflecting the nature of drug medical content, showing the number of times "Hospital 1" has prescribed and recommended the drug.

Naturally, other information may be displayed in indicator popups. For example, indicator popups may show condition or symptom information, side effect data, board certifications, specialties, provider rankings, or other information that may be used to understand the basis for ranking indicators or provide more detail to a user. The information in indicator popups will, of course, vary by the nature and type of indicator used shown in the results presentation. Use of the term "indicator popups" is not intended to be limiting of the type and manner of presenting additional information about an indicator. Many other types of interface elements are possible, as will be appreciated by practitioners in the art.

An aggregation of information can also be presented so that other search engines and databases, including those available through a search engine like Google™ and Bing®, can be performed and the results presented side-by-side together.

Figure 4:
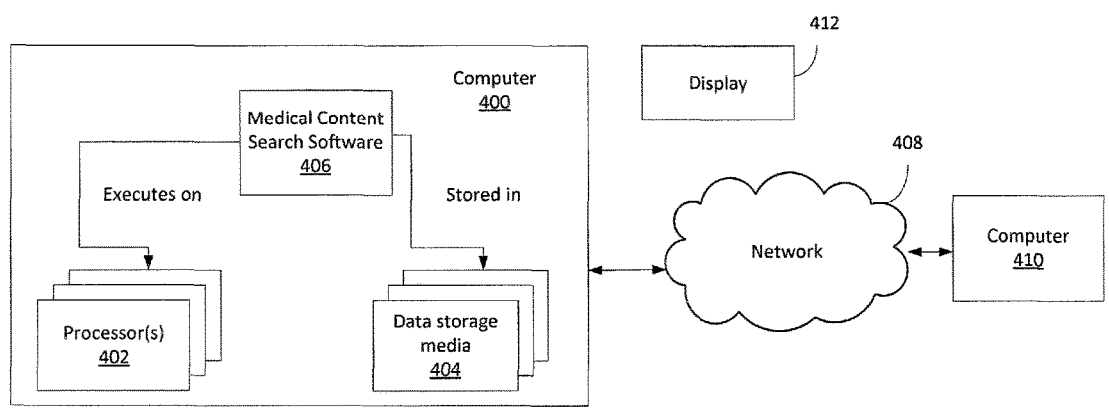
FIG. 4 is a block diagram of example components that may be used in connection with implementations of the subject matter described herein.

FIG. 4 shows an example environment in which aspects of the subject matter described herein may be deployed.

Computer 400 includes one or more processors 402 and one or more data storage media 404. Processor(s) 402 are typically microprocessors, such as those found in a personal desktop or laptop computer, smartphone, tablet, a server, a handheld computer, or another kind of computing device. Data storage media 404 are components that are capable of storing data for either the short or long term. Examples of data storage media 404 include, but are not limited to, hard disks, removable disks (including optical and magnetic disks), volatile and non-volatile random-access memory (RAM), read-only memory (ROM), flash memory, magnetic tape, and the like. The data storage media may also include other computer-readable storage media; however it should be understood that the data storage media and computer-readable storage media do not include propagating signals and carrier waves.

The computer 400 may include, or be associated with, display 412, which may be a cathode ray tube (CRT) monitor, a liquid crystal display (LCD) monitor, or any other type of monitor or display device.

Software may be stored in the data storage media 404. The software can be executed by the one or more processor(s) 402. An example of such software is medical content search software 406, which may implement some or all of the functionality described herein, although any type of software could be used. Software 406 may be implemented, for example, through one or more components, which may be components in a distributed system, separate files, separate functions, separate objects, separate lines of code, etc.

A computer (e.g., personal computer, server computer, handheld computer, smartphone, tablet) in which a program is stored on hard disk (or solid state drive or other storage media), loaded into RAM, and executed on the computer's processor(s) typifies the scenario depicted in FIG. 4, although the subject matter described herein is not limited to this example.

The subject matter described herein can be implemented as software that is stored in one or more of the data storage media 404 (or computer-readable storage media) and that executes on one or more of the processor(s) 402. The instructions to perform the acts could be stored on one medium, or could be spread out across plural media, so that the instructions might appear collectively on the one or more computer-readable storage media, regardless of whether all of the instructions happen to be on the same medium. It is noted that there is a distinction between media on which signals are "stored" (which may be referred to as "storage media"), and—in contradistinction—media that contain or transmit propagating signals. DVDs, flash memory, magnetic disks, etc., are examples of storage media. On the other hand, wires or fibers on which signals exist ephemerally are examples of transitory signal media. Thus, it will be understood that a storage media is non-transitory.

Additionally, any acts described herein (whether or not shown in a diagram) may be performed by a processor (e.g., one or more processors 402) as part of a method. Thus, if the acts A, B, and C are described herein, then a method may be performed that comprises the acts of A, B, and C. Moreover, if the acts of A, B, and C are described herein, then a method may be performed that comprises using a processor to perform the acts of A, B, and C. In one example environment, computer 400 may be communicatively connected to one or more other devices through network 408. Computer 410, which may be similar in structure to computer 400, is an example of a device that can be connected to computer 400, although other types of devices may also be so connected.

It should be understood that the examples and embodiments described herein are for illustrative purposes only and that various modifications or changes in light thereof will be suggested to persons skilled in the art and are to be included within the spirit and purview of this application.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

All patents, patent applications, provisional applications, and publications referred to or cited herein are incorporated by reference in their entirety, including all figures and tables, to the extent they are not inconsistent with the explicit teachings of this specification.

What is claimed is:

1. A computer-based medical content search and results generation system, the system comprising:
    one or more non-transitory computer readable storage media having processor executable instructions stored thereon;
    a medical content database or table stored on the one or more non-transitory computer readable storage media; and
    a medical content search and ranking engine that, when executed by one or more processors, directs the one or more processors to:
    provide a graphical user interface that displays a search input field distinct from at least one drop down menu, wherein the at least one drop down menu provides a plurality of search filter parameters for filtering by medical condition, filtering by symptom, filtering by content type, or filtering by healthcare provider;
    receive a search query for medical content;
    perform a search for medical content constrained by the search query;
    identify a plurality of medical content from the medical content database in response to the search query;
    identify a number of times each medical content of the plurality of medical content has been referenced by healthcare providers of a set of at least one designated healthcare provider;
    transmit a search result of the plurality of medical content that is ordered based on the number of times each medical content has been referenced; and
    display on the graphical user interface a vertical search result of the plurality of medical content that is ordered based on the number of times each medical content has been referenced, wherein each respective medical content of the plurality of medical content has horizontal to it at least one respective healthcare provider indicator for each respective healthcare provider that referenced the respective medical content;

wherein each respective healthcare provider indicator comprises information of the respective healthcare provider;

wherein each healthcare provider indicator is linked to a popup that displays information of the respective healthcare provider;

wherein displaying on the graphical user interface a vertical search result of the plurality of medical content that is ordered based on the number of times each medical content has been referenced comprises:

displaying a search result of a plurality of medical content wherein at least one medical content of the plurality of medical content is a medical device, medical equipment, drug, medical product, pharmaceutical, medical procedure, medical therapy, or medical treatment; and ordering the vertical search result with most referenced content first and breaking ties by at least one tie-breaker from the group consisting of:

average ranking by at least one ranking organization for the healthcare providers that reference the medical content, the medical content type, credentials of healthcare providers that reference the medical content, recency of the references, incidence of side-effects caused by the medical content, a user's medical history, and a user's option selection; and wherein the vertical search result of the plurality of medical content that is ordered based on the number of times each medical content has been referenced is displayed to a side of, and grouped for, a respective medical condition, wherein the respective medical condition is one of a vertically ordered plurality of medical conditions, and wherein each respective medical condition of the vertically ordered plurality of medical conditions has a respective vertical search result of a plurality of medical content that is ordered based on the number of times each medical content has been referenced to the side of, and grouped for, the respective medical condition, and wherein each respective medical content has horizontal to it at least one respective healthcare provider indicator for each respective healthcare provider that referenced the respective medical content.

2. The system of claim 1, wherein receiving the search query comprises receiving at least one search term.

3. A computer-based medical content search and results generation system, the system comprising:

one or more non-transitory computer readable storage media having processor executable instructions stored thereon;

a medical content database or table stored on the one or more non-transitory computer readable storage media; and a medical content search and ranking engine that, when executed by one or more processors, directs the one or more processors to:

provide a graphical user interface that displays a search input field distinct from at least one drop down menu, comprising a drop down menu that provides a plurality of search filter parameters for filtering by medical condition, filtering by symptom, filtering by content type, or filtering by healthcare provider;

receive a search query for medical content;

perform a search for medical content constrained by the search query and search filter parameters;

identify a plurality of medical content from the medical content database in response to the search query;

identify a number of times each medical content of the plurality of medical content has been referenced by healthcare providers of a set of at least one designated healthcare provider;

transmit a search result of the plurality of medical content that is ordered based on the number of times each medical content has been referenced; and display on the graphical user interface a vertical search result of the plurality of medical content that is ordered based on the number of times each medical content has been referenced;

wherein each respective medical content of the plurality of medical content has horizontal to it at least one respective healthcare provider indicator for each respective healthcare provider that referenced the respective medical content;

wherein each respective healthcare provider indicator comprises information of the respective healthcare provider;

wherein each healthcare provider indicator is linked to a popup that displays information of the respective healthcare provider;

wherein displaying on the graphical user interface a vertical search result of the plurality of medical content that is ordered based on the number of times each medical content has been referenced comprises:

displaying a search result of a plurality of medical content wherein at least one medical content of the plurality of medical content is a medical device, medical equipment, drug, medical product, pharmaceutical, medical procedure, medical therapy, or medical treatment; and ordering the vertical search result with most referenced content first and breaking ties by at least one tie-breaker from the group consisting of:

average ranking by at least one ranking organization for the healthcare providers that reference the medical content, the medical content type, credentials of healthcare providers that reference the medical content, recency of the references, incidence of side-effects caused by the medical content, a user's medical history, and a user's option selection; and wherein the vertical search result of the plurality of medical content that is ordered based on the number of times each medical content has been referenced is displayed to a side of, and grouped for, a respective medical condition, wherein the respective medical condition is one of a vertically ordered plurality of medical conditions, and wherein each respective medical condition of the vertically ordered plurality of medical conditions has a respective vertical search result of a plurality of medical content that is ordered based on the number of times each medical content has been referenced to the side of, and grouped for, the respective medical condition, and wherein each respective medical content has horizontal to it at least one respective healthcare provider indicator for each respective healthcare provider that referenced the respective medical content.

4. The system of claim 1, wherein receiving the search query comprises receiving data from a biometric sensor; and wherein a single healthcare provider can only contribute a maximum of one healthcare provider indicator, for a single medical content, even if a single healthcare provider has multiple references for the single medical content within a specific filtered time frame, and wherein the set of at least one designated healthcare provider comprises a set controlled for by the user.

5. The system of claim 1, wherein the set of at least one designated healthcare provider comprises at least one medical facility, hospital, pharmacy, doctor, or healthcare professional; and wherein a single healthcare provider can only contribute a maximum of one healthcare provider indicator, for a single medical content, even if a single healthcare provider has multiple references for the single ranked medical content within a specific filtered time frame.

6. The system of claim 1, wherein identifying the plurality of medical content comprises searching a database of medical content organized by medical condition, symptom, and side effect; and wherein a single healthcare provider can only contribute a maximum of one healthcare provider indicator to a single content.

7. The system of claim 1, wherein identifying the plurality of medical content comprises searching a database of medical content by one or more of medical content name, medical condition, symptom, and side effect;

wherein a single healthcare provider can only contribute a maximum of one healthcare provider indicator, for a single medical content, even if a single healthcare provider has multiple references for the single medical content within a specific filtered time frame; and wherein the set of at least one designated healthcare provider comprises a set controlled for by a user.

8. The system of claim 1, wherein identifying the number of times each medical content of the plurality of medical content has been referenced comprises:

identifying the number of times each medical content of the plurality of medical content has been purchased, used, prescribed, and recommended by each healthcare provider or combination of healthcare providers; and wherein a single healthcare provider can contribute an unlimited amount of healthcare provider indicators to a single content.

9. A computer-based medical content search and results generation system, the system comprising:

one or more non-transitory computer readable storage media having processor executable instructions stored thereon;

a medical content database or table stored on the one or more non-transitory computer readable storage media; and a medical content search and ranking engine that, when executed by one or more processors, directs the one or more processors to:

receive a search query for medical content;

perform a search for medical content constrained by the search query or search filter parameters;

identify a plurality of medical content from the medical content database in response to the search query;

identify a number of times each medical content of the plurality of medical content has been referenced by healthcare providers of a set of at least one designated healthcare provider;

transmit a search result of the plurality of medical content that is ordered based on the number of times each medical content has been referenced; and display on the graphical user interface a vertical search result of the plurality of medical content that is ordered based on the number of times each medical content has been referenced;

wherein each respective medical content of the plurality of medical content has horizontal to it at least one respective healthcare provider indicator for each respective healthcare provider that referenced the respective medical content;

wherein each respective healthcare provider indicator comprises information of the respective healthcare provider;

wherein each healthcare provider indicator is linked to a popup that displays information of the respective healthcare provider;

wherein displaying on the graphical user interface a vertical search result of the plurality of medical content that is ordered based on the number of times each medical content has been referenced comprises displaying a search result of a plurality of medical content wherein at least one medical content of the plurality of medical content is a medical device, medical equipment, drug, medical product, pharmaceutical, medical procedure, medical therapy, or medical treatment; and wherein the vertical search result of the plurality of medical content that is ordered based on the number of times each medical content has been referenced is displayed to a side of, and grouped for, a respective medical condition, wherein the respective medical condition is one of a vertically ordered plurality of medical conditions, and wherein each respective medical condition of the vertically ordered plurality of medical conditions has a respective vertical search result of a plurality of medical content that is ordered based on the number of times each medical content has been referenced to the side of, and grouped for, the respective medical condition, and wherein each respective medical content has horizontal to it at least one respective healthcare provider indicator for each respective healthcare provider that referenced the respective medical content.

10. The system of claim 9, wherein receiving the search query comprises receiving at least one term; and wherein a single healthcare provider can only contribute a maximum of one healthcare provider indicator, for a single medical content, even if a single healthcare provider has multiple references for the single medical content within a specific filtered time frame;

wherein the set of at least one designated healthcare provider comprises a set controlled for by the user; and wherein the information of the respective healthcare provider that each respective healthcare provider indicator comprises is a name of the respective healthcare provider.

11. The system of claim 9, wherein the graphical user interface displays a search input field that is distinct from at least one drop down menu, wherein the at least one drop down menu provides for filtering by medical condition, filtering by symptom, filtering by medical content type, or filtering by healthcare provider;

wherein the set of at least one designated healthcare provider comprises at least one medical facility, healthcare professional, doctor, hospital, or pharmacy, wherein receiving the search query comprises receiving a hypertext transfer protocol (HTTP) request for a webpage, and wherein a single healthcare provider can only contribute a maximum of one healthcare provider indicator to a single content.

12. The system of claim 3, wherein receiving the search query comprises receiving data from a biometric sensor; and
wherein a single healthcare provider can only contribute a maximum of one healthcare provider indicator to a single content.

13. The system of claim 9, wherein the set of at least one healthcare provider comprises at least one of a medical facility, hospital, pharmacy, doctor, and healthcare professional; and
wherein a single healthcare provider can contribute an unlimited amount of healthcare provider indicators to a single content.

14. The system of claim 9, wherein the medical content database or table comprises medical content organized by medical content name, medical condition, symptom, and side effect.

15. The system of claim 14, wherein identifying the plurality of medical content comprises searching the medical content database or table by one or more of medical content name, medical condition, symptom, and side effect; and
wherein a single healthcare provider can only contribute a maximum of one reference and a maximum of one healthcare provider indicator, for a single medical content, even if a single healthcare provider has multiple references for the single medical content within a specific filtered time frame.

16. The system of claim 9, wherein identifying the number of times each medical content of the plurality of medical content has been referenced comprises:
identifying the number of times each medical content of the plurality of medical content has been purchased, used, prescribed, and recommended by each healthcare provider or combination of healthcare providers.

17. The system of claim 9, wherein displaying on the graphical user interface a vertical search result of the plurality of medical content that is ordered based on the number of times each medical content has been referenced comprises:
ordering the search result with most referenced content first and breaking ties by at least one tie-breaker from the group consisting of:
average ranking by at least one ranking organization for the healthcare providers that reference the content;
the medical content type;
credentials of healthcare providers that reference the medical content;
recency of the references;
incidence of side-effects caused by the medical content; and
a user's option selection.

18. A method of conducting a computer-based medical content search comprising:
accessing a computer-based medical content search and results generation system according to claim 1,
conducting a medical content search on said system, and obtaining results of the search.

19. A method of conducting a computer-based medical content search comprising:
accessing a computer-based medical content search and results generation system according to claim 3,
conducting a medical content search on said system, and obtaining results of the search.

20. A method of conducting a computer-based medical content search comprising:
accessing a computer-based medical content search and results generation system according to claim 9,
conducting a medical content search on said system, and obtaining results of the search.

* * * * *